US011039254B2

(12) United States Patent
Ye

(10) Patent No.: US 11,039,254 B2
(45) Date of Patent: Jun. 15, 2021

(54) MEMS-BASED BONE CONDUCTION SENSOR

(71) Applicants: ZILLTEK TECHNOLOGY (SHANGHAI) CORP., Shanghai (CN); ZILLTEK TECHNOLOGY CORP., Hsinchu (TW)

(72) Inventor: Jinghua Ye, Shanghai (CN)

(73) Assignees: ZILLTEK TECHNOLOGY (SHANGHAI) CORP., Shanghai (CN); ZILLTEK TECHNOLOGY CORP., Hsinchu (TW)

( * ) Notice: Subject to any disclaimer, the term of this patent is extended or adjusted under 35 U.S.C. 154(b) by 0 days.

(21) Appl. No.: 16/661,326

(22) Filed: Oct. 23, 2019

(65) Prior Publication Data

US 2020/0288250 A1 Sep. 10, 2020

(30) Foreign Application Priority Data

Mar. 7, 2019 (CN) ......................... 201910173096.4

(51) Int. Cl.
*A61F 11/06* (2006.01)
*H04R 19/02* (2006.01)
(Continued)

(52) U.S. Cl.
CPC ....... *H04R 19/02* (2013.01); *G10K 11/17854* (2018.01); *G10K 11/17873* (2018.01);
(Continued)

(58) Field of Classification Search
CPC .......... H04R 19/02; H04R 1/10; H04R 1/406; H04R 3/005; H04R 2201/003;
(Continued)

(56) References Cited

U.S. PATENT DOCUMENTS

2017/0064427 A1* 3/2017 Rich .................... H04R 1/1025

FOREIGN PATENT DOCUMENTS

CN 106686494 A 5/2017
CN 107277723 A 10/2017

OTHER PUBLICATIONS

Sonion (Humanizing the Digital Experience, TDK Developers Conference, Sep. 17-8, 2018) (Year: 2018).*

* cited by examiner

*Primary Examiner* — Ammar T Hamid
(74) *Attorney, Agent, or Firm* — Calfee Halter & Griswold LLP

(57) ABSTRACT

The invention relates to the field of electronic technology, and more particularly, to a microphone structure. A MEMS (Micro-Electro-Mechanical System)-based bone conduction sensor comprises: a closed cavity within which a uniaxial or biaxial accelerometer sensor is arranged to be adjacent to bones of a human ear; an ASIC (application-specific integrated circuit) processing chip coupled to the uniaxial or biaxial accelerometer sensor, the ASIC processing chip being provided with an output end for a vibration signal. By adopting the above-mentioned technical solution, a bone conduction sensor with a closed cavity is provided in the present invention. Furthermore, a uniaxial or biaxial accelerometer sensor and an ASIC processing chip are arranged inside the closed cavity. In this way, the production costs are reduced, and interference of the sensor caused by ambient environment is reduced.

12 Claims, 1 Drawing Sheet

(51) Int. Cl.

*G10K 11/178* (2006.01)
*G10L 19/00* (2013.01)
*H04R 1/10* (2006.01)
*H04R 3/00* (2006.01)
*H04R 1/40* (2006.01)

(52) U.S. Cl.

CPC ................ *G10L 19/00* (2013.01); *H04R 1/10* (2013.01); *H04R 1/406* (2013.01); *H04R 3/005* (2013.01); *G10K 2210/1081* (2013.01); *G10K 2210/3028* (2013.01); *H04R 2201/003* (2013.01); *H04R 2420/07* (2013.01); *H04R 2460/01* (2013.01); *H04R 2460/13* (2013.01)

(58) Field of Classification Search

CPC ............ H04R 2420/07; H04R 2460/01; H04R 2460/13; G10K 11/17854; G10K 2210/1081; G10K 2210/3028; G10K 11/17873; G10L 19/00

USPC ....................................... 381/71.6, 312, 72.1

See application file for complete search history.

MEMS-BASED BONE CONDUCTION SENSOR

CROSS-REFERENCE TO RELATED APPLICATIONS

The present application claims priority to and the benefit of Chinese Patent Application No. CN 201910173096.4 filed on Mar. 7, 2019, the entire content of which is incorporated herein by reference.

BACKGROUND OF THE INVENTION

1. Field of the Invention

The invention relates to the field of electronic technology, and more particularly, to a microphone structure.

2. Description of the Related Art

MEMS (Micro-Electro-Mechanical System) microphones are fabricated using MEMS technology, in other words, a capacitor is integrated into a micro silicon wafer. The MEMS microphones can be made by surface-mount technology and capable of withstanding an extremely high solder-reflow temperature; it is easy for them to be integrated with CMOS (Complementary Metal OXIDE Semiconductor) technology and other audio circuits; and it has an improved ability to eliminate and suppress noise. Conventional MEMS microphones have some problems listed below. They only capture sound waves generated from the people's vocal cord vibration when speaking, and the sound waves propagate though a medium (which refers to air). However, the sound waves are always interrupted by ambient noise during their propagation, which may greatly reduce voice call quality. Therefore, it may be difficult to achieve a high signal-to-noise ratio in such a microphone that sound waves are captured by sound sensing elements.

In order to improve performances of the microphones, the prior art adopts a G-sensor (Accelerometer-sensor) as a bone conduction sensor. The G-sensor is one of the MEMS sensors. It can detect changes in acceleration. For example, shaking, falling off, rising up, lowering down and other movements may be converted into electric signals by the G-sensor. Moreover, finger sets are provided inside the G-sensor for measuring the displacement of a mass block when the acceleration is generated. Each of the finger sets corresponds to two capacitor plates. When there is acceleration, the mass bock may produce relative movement, and changes of displacement may result in the change of differential capacitance. Then detection of the differential capacitance and calculation of acceleration are done inside the G-sensor, and an output value is obtained. The G-sensor measures the movement of three axial objects in a three-dimensional Cartesian coordinate system, and the microphone here detects the people's vibration of bones when speaking. When compared with the conventional accelerometer sensors, the inclusion of a gravity accelerometer sensor and an intelligent gravity sensing system in the G-sensor may result in the increase of manufacturing costs of hearing aids and Bluetooth headsets and other related products. Therefore, it may be difficult for manufacturers to improve product quality and meet the requirements of customers while keeping the manufacturing costs down.

SUMMARY OF THE INVENTION

The objective of the present invention is to provide a MEMS (Micro-Electro-Mechanical System)-based bone conduction sensor so as to solve the previously mentioned technical problems.

The objective may be achieved by using the following technical solution:

A MEMS-based bone conduction sensor disposed on an ear-mounted device, the MEMS-based bone conduction sensor comprising:

a closed cavity, within which the following components are disposed:

a uniaxial or biaxial accelerometer sensor arranged to be adjacent to bones of a human ear;

an ASIC (application-specific integrated circuit) processing chip coupled to the uniaxial or biaxial accelerometer sensor, the ASIC processing chip being provided with an output end for a vibration signal.

An ear-mounted device, comprising:

a primary microphone for sensing sound wave signals;

a secondary microphone spaced from the primary microphone by a set distance;

an audio codec coupled to the primary microphone and the secondary microphone; and a microcontroller coupled to a signal output end of the bone conduction sensor and to a signal input end of the audio codec.

In some embodiments, air, vacuum, or other gases are contained in the closed cavity.

In some embodiments, the bone conduction sensor comprises at least one acoustic sensor, the acoustic sensor comprises a back plate and a vibrating diaphragm, and the vibrating diaphragm is used to sense the vibration signal.

In some embodiments, the ear-mounted device comprises a hearing aid or a Bluetooth headset.

In some embodiments, the ear-mounted device further comprises a time division multiplexing circuit, wherein an input interface of the time division multiplexing circuit is connected to an output end of the bone conduction sensor and to output ends of the primary microphone and the secondary microphone, and an output end of the time division multiplexing circuit is connected to an input end of the microcontroller.

In some embodiments, the audio codec comprises an adaptive filter for noise cancellation of a converted audio signal and for enhancement of the audio signal subjected to the noise cancellation.

In some embodiments, the audio codec comprises a loudspeaker connected to an output end of the audio codec.

Beneficial effects: by adopting the above-mentioned technical solution, a MEMS-based bone conduction sensor with a closed cavity is provided in the present invention. Furthermore, a uniaxial or biaxial accelerometer sensor and an ASIC processing chip are arranged inside the closed cavity. In this way, the production costs are reduced, and interference of the sensor caused by ambient environment is reduced.

BRIEF DESCRIPTION OF THE DRAWINGS

The accompanying drawings, together with the specification, illustrate exemplary embodiments of the present disclosure, and, together with the description, serve to explain the principles of the present invention.

DETAILED DESCRIPTION

Figure 1:
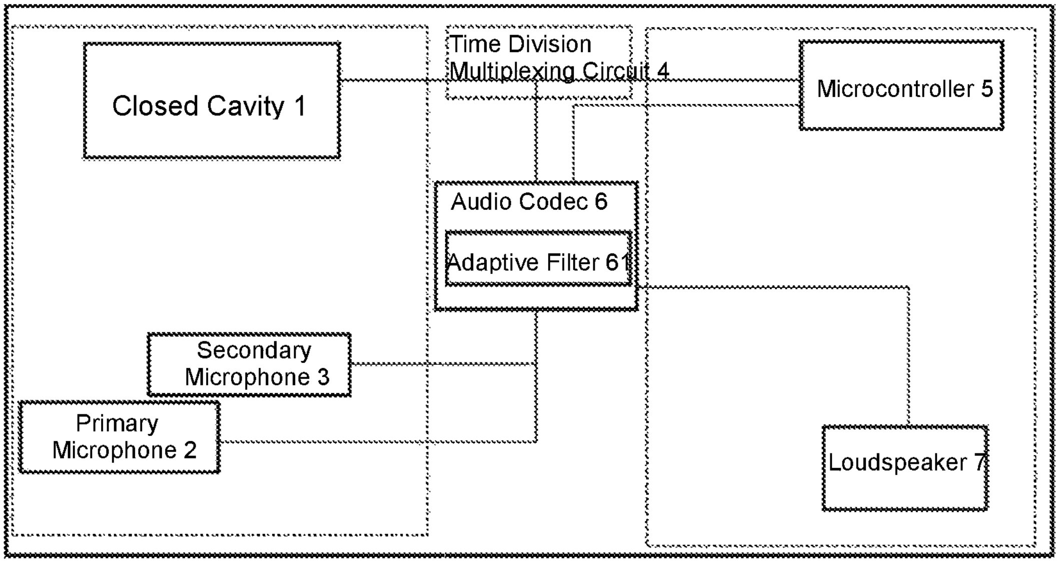
FIG. 1 is a schematic diagram showing a circuit connection of an embodiment according to the present invention.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "plurality" means a number greater than one.

Hereinafter, certain exemplary embodiments according to the present disclosure will be described with reference to the accompanying drawings.

Figure 2:
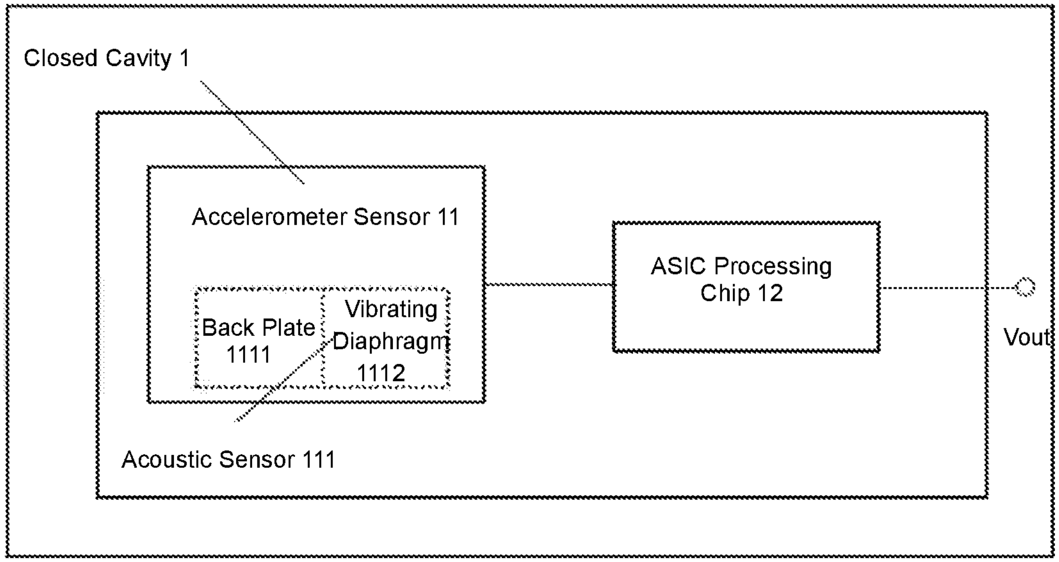
FIG. 2 is a schematic diagram showing part of a circuit connection of an embodiment according to the present invention.

Referring to FIG. 1, A MEMS-based bone conduction sensor, comprising:

a primary microphone 2 for sensing sound wave signals;

a secondary microphone 3 spaced from the primary microphone 1 by a set distance, and configured for sensing the sound wave signals;

an audio codec 6 coupled to the primary microphone 2 and the secondary microphone 3;

a microcontroller coupled to a signal output end of the closed cavity 1 and to a signal input end of the audio codec 6;

a closed cavity 1 within which the following components are disposed, as shown in FIG. 2:

a uniaxial or biaxial accelerometer sensor 11 arranged to be adjacent to bones of a human ear; an ASIC (application-specific integrated circuit) processing chip 12 coupled to the uniaxial or biaxial accelerometer sensor 11, the ASIC processing chip 12 being provided with an output end for a vibration signal.

As an embodiment of the present invention, the bone conduction sensor further comprises a time division multiplexing circuit 4. An input end of the time division multiplexing circuit 4 is connected to the closed cavity 1, the primary microphone 2 and the secondary microphone 3, and an output end thereof is connected to the microprocessor 5, such that vibration signals captured by the uniaxial or biaxial accelerometer sensor 11 and the sound wave signals detected by the primary microphone 2 and the secondary microphone 3 may be transmitted simultaneously in one channel.

The time division multiplexing circuit 4 provides a single interface for a plurality of devices. As a result, complexity for circuit connection is reduced, demand for RAM is reduced, and power consumption on a host computer is decreased.

As an embodiment of the present invention, air, vacuum, or other gases are contained in the closed cavity 1 so as to reduce disturbance of the uniaxial or biaxial accelerometer sensor 11 caused by ambient environment, thereby improving voice quality. In addition, the structure of the closed cavity solves the problem that the G-sensor in the prior art has the shortcoming of high costs, thus, the manufacturing cost of the manufactures is reduced, and mass production is possible.

As an embodiment of the present invention, the uniaxial or biaxial accelerometer sensor 11 comprises at least one acoustic sensor 111, the acoustic sensor 111 comprises a back plate 1111 and a vibrating diaphragm 1112, and the vibrating diaphragm 1112 is used to sense the vibration signal.

As an embodiment of the present invention, the audio codec 6 comprises an adaptive filter 61 for noise cancellation of a converted audio signal and for enhancement of the audio signal subjected to the noise cancellation.

As an embodiment of the present invention, the signal output end of the closed cavity 1 is provided with a specific time division multiplexing circuit interface for connection with the input end of the time division circuit.

As an embodiment of the present invention, the ear-mounted device formed of this circuit structure may comprises a hearing aid or a Bluetooth headset.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A MEMS (Micro-Electro-Mechanical System)-based bone conduction sensor, disposed on an ear-mounted device, the MEMS-based bone conduction sensor comprising:

a closed cavity, within which the following components are disposed: a uniaxial or biaxial accelerometer sensor arranged to be adjacent to bones of a human ear;

an ASIC (application-specific integrated circuit) processing chip coupled to the uniaxial or biaxial accelerometer sensor, the ASIC processing chip being provided with an output end for a vibration signal;

vacuum is contained in the cavity, the ASIC processing chip is provided with a time division multiplexing circuit interface.

2. The MEMS-based bone conduction sensor of claim 1, wherein the bone conduction sensor comprises at least one acoustic sensor, the acoustic sensor comprises a back plate and a vibrating diaphragm, and the vibrating diaphragm is configured to sense the vibration signal.

3. The MEMS-based bone conduction sensor of claim 1, wherein the ear-mounted device comprises a hearing aid or a Bluetooth headset.

4. An ear-mounted device comprising the bone conduction sensor of claim 1, further comprising:

a primary microphone for sensing sound wave signals;

a secondary microphone spaced from the primary microphone by a set distance;

an audio codec coupled to the primary microphone and the secondary microphone;

a microcontroller coupled to a signal output end of the bone conduction sensor and to a signal input end of the audio codec; and a time division multiplexing circuit, wherein an input interface of the time division multiplexing circuit is connected to an output end of the bone conduction sensor and to output ends of the primary microphone and the secondary microphone, and an output end of the time division multiplexing circuit is connected to an input end of the microcontroller.

5. The ear-mounted device of claim 4, wherein the audio codec comprises an adaptive filter for noise cancellation of a converted audio signal and for enhancement of the audio signal subjected to the noise cancellation.

6. The ear-mounted device of claim 4, further comprising:

a loudspeaker connected to an output end of the audio codec.

7. An ear-mounted device comprising the bone conduction sensor of claim 2, further comprising:

a primary microphone for sensing sound wave signals;

a secondary microphone spaced from the primary microphone by a set distance;

an audio codec coupled to the primary microphone and the secondary microphone;

a microcontroller coupled to a signal output end of the bone conduction sensor and to a signal input end of the audio codec; and a time division multiplexing circuit, wherein an input interface of the time division multiplexing circuit is connected to an output end of the bone conduction sensor and to output ends of the primary microphone and the secondary microphone, and an output end of the time division multiplexing circuit is connected to an input end of the microcontroller.

8. The ear-mounted device of claim 7, wherein the audio codec comprises an adaptive filter for noise cancellation of a converted audio signal and for enhancement of the audio signal subjected to the noise cancellation.

9. The ear-mounted device of claim 7, further comprising:

a loudspeaker connected to an output end of the audio codec.

10. An ear-mounted device comprising the bone conduction sensor of claim 1, further comprising:

a primary microphone for sensing sound wave signals;

a secondary microphone spaced from the primary microphone by a set distance;

an audio codec coupled to the primary microphone and the secondary microphone;

a microcontroller coupled to a signal output end of the bone conduction sensor and to a signal input end of the audio codec; and a time division multiplexing circuit, wherein an input interface of the time division multiplexing circuit is connected to an output end of the bone conduction sensor and to output ends of the primary microphone and the secondary microphone, and an output end of the time division multiplexing circuit is connected to an input end of the microcontroller.

11. The ear-mounted device of claim 10, wherein the audio codec comprises an adaptive filter for noise cancellation of a converted audio signal and for enhancement of the audio signal subjected to the noise cancellation.

12. The ear-mounted device of claim 10, further comprising:

a loudspeaker connected to an output end of the audio codec.

* * * * *